(12) United States Patent
Iwamoto et al.

(10) Patent No.: US 8,946,286 B2
(45) Date of Patent: Feb. 3, 2015

(54) ORGANIC AMINE SALTS OF AMINOBENZOIC ACID DERIVATIVES AND METHOD FOR PRODUCING SAME

(75) Inventors: Shunsuke Iwamoto, Funabashi (JP); Satoshi Nakano, Funabashi (JP); Mariko Ishida, Funabashi (JP); Masao Yamamoto, Tokyo (JP); Kazuya Takeuchi, Shiraoka (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 13/883,171

(22) PCT Filed: Nov. 1, 2011

(86) PCT No.: PCT/JP2011/075218
§ 371 (c)(1),
(2), (4) Date: May 2, 2013

(87) PCT Pub. No.: WO2012/060388
PCT Pub. Date: May 10, 2012

(65) Prior Publication Data
US 2013/0217894 A1   Aug. 22, 2013

(30) Foreign Application Priority Data

Nov. 2, 2010   (JP) .................................. 2010-246632

(51) Int. Cl.
| | | |
|---|---|---|
| *A61K 31/38* | (2006.01) | |
| *C07D 333/32* | (2006.01) | |
| *A61K 9/00* | (2006.01) | |
| *A61K 47/14* | (2006.01) | |
| *A61K 9/16* | (2006.01) | |
| *A61K 9/20* | (2006.01) | |
| *A61K 9/48* | (2006.01) | |

(52) U.S. Cl.
CPC ............ *C07D 333/32* (2013.01); *A61K 9/0019* (2013.01); *A61K 47/14* (2013.01); *A61K 9/1623* (2013.01); *A61K 9/1652* (2013.01); *A61K 9/2018* (2013.01); *A61K 9/2059* (2013.01); *A61K 9/4866* (2013.01)
USPC ........................................... 514/445; 549/65

(58) Field of Classification Search
CPC .............................. A61K 47/12; C07D 333/12
USPC .............................................................. 549/65
See application file for complete search history.

(56) References Cited

U.S. PATENT DOCUMENTS

| | | | | |
|---|---|---|---|---|
| 2,774,759 | A | * | 12/1956 | Blackett et al. ................ 544/261 |
| 5,663,444 | A | * | 9/1997 | Melder et al. .................. 524/477 |
| 2004/0058990 | A1 | | 3/2004 | Duffy et al. |
| 2006/0094694 | A1 | | 5/2006 | Owada et al. |
| 2010/0310537 | A1 | | 12/2010 | Nakamura et al. |

FOREIGN PATENT DOCUMENTS

| | | | |
|---|---|---|---|
| CN | 1798739 A | | 7/2006 |
| JP | 2000/288081 | * | 10/2000 |
| JP | 2006 527187 | | 11/2006 |
| WO | 99/20106 | * | 4/1999 |
| WO | 02 49413 | | 6/2002 |
| WO | 2004 108683 | | 12/2004 |
| WO | 2007/096588 | * | 8/2007 |
| WO | 2009 072626 | | 6/2009 |

OTHER PUBLICATIONS

Combined Office Action and Search Report issued Nov. 29, 2013 in Chinese Application No. 201180049049.0 (With English Translation).

International Search Report Issued Dec. 6, 2011 in PCT/JP11/75218 Filed Nov. 1, 2011.

* cited by examiner

*Primary Examiner* — Taofiq A Solola
(74) *Attorney, Agent, or Firm* — Oblon, Spivak, McClelland, Maier & Neustadt, L.L.P.

(57) ABSTRACT

A novel organic amine salt or salt with quaternary ammonium ion of 3-{[((2E)-2-{1-[5-(4-t-butylphenyl)-4-hydroxy-3-thienyl]ethylidene}hydrazino)carbonothioyl]
amino}benzoic acid having useful properties as a drug is provided.

A novel organic amine or salt with quaternary ammonium ion of 3-{[((2E)-2-{1-[5-(4-t-butylphenyl)-4-hydroxy-3-thienyl]ethylidene}hydrazino)carbonothioyl]amino}benzoic acid, a method for producing the organic amine salt or the salt with quaternary ammonium ion and a platelet increasing agent.

18 Claims, 1 Drawing Sheet

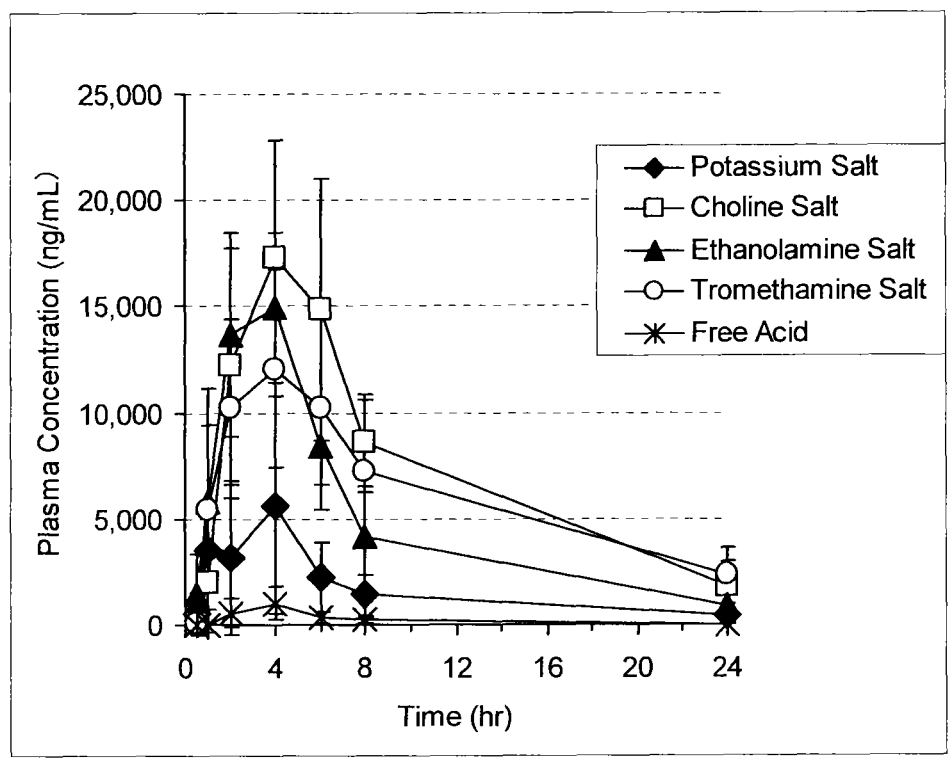

ORGANIC AMINE SALTS OF AMINOBENZOIC ACID DERIVATIVES AND METHOD FOR PRODUCING SAME

CROSS-REFERENCE TO RELATED APPLICATIONS

This application is a National Stage of PCT/JP2011/075218 filed on Nov. 1, 2011. This application is based upon and claims the benefit of priority to Japanese Application No. 2010-246632 filed on Nov. 2, 2010, the entire contents of which are incorporated herein by reference.

BACKGROUND OF THE INVENTION

1. Technical Field

The present invention relates to novel thrombopoietin receptor activators, which are organic amine salts of 3-{[((2E)-2-{1-[5-(4-t-butylphenyl)-4-hydroxy-3-thienyl]ethylidene}hydrazino)carbonothioyl]amino}benzoic acid. The compounds of the present invention are useful as therapeutic agents for diseases accompanied by abnormal platelet counts or platelet increasing agents.

2. Background Art

3-{[((2E)-2-{1-[5-(4-t-Butylphenyl)-4-hydroxy-3-thienyl]ethylidene}hydrazino)carbonothioyl]amino}benzoic acid (hereinafter referred to as Compound A) is useful as a thrombopoietin receptor activator. Compound A is disclosed in WO04/108683 (Patent Document 1) and JP-A-2006-527187 (Patent Document 2) as a compound encompassed by a general formula along with its tautomers, prodrugs or pharmaceutically acceptable salts or solvates thereof. Compound A is disclosed in US 2006/094694 A1 (Patent Document 3) as a specific compound. Regarding salts of Compound A, although alkali metal salts and the like are mentioned as pharmaceutically acceptable salts, no specific salts are disclosed as working examples.

PRIOR ART DOCUMENT

Patent Document 1: WO04/108683
Patent Document 2: JP-A-2006-527187
Patent Document 3: US 2006/094694 A1

DISCLOSURE OF INVENTION

Technical Problem

An object of the present invention is to provide novel salts of 3-{[((2E)-2-{1-[5-(4-t-butylphenyl)-4-hydroxy-3-thienyl]ethylidene}hydrazino)carbonothioyl]amino}benzoic acid which have useful properties such as better pharmacokinetic properties and stability as compared with the free form and alkali metal salts of it and medicines containing them as active ingredients. Another object of the present invention is to provide a method for producing the above-mentioned novel salts.

Solution to Problems

As a result of extensive research to solve the above-mentioned problems, the present inventors have found novel organic amine salts or quaternary ammonium salts of 3-{[((2E)-2-{1-[5-(4-t-butylphenyl)-4-hydroxy-3-thienyl]ethylidene}hydrazino)carbonothioyl]amino}benzoic acid, medicines containing the said organic amine salts or quaternary ammonium salts as active ingredients and a method for producing the said organic amine salts or quaternary ammonium salts. Surprisingly, these organic amine salts or quaternary ammonium salts have advantages useful when used as therapeutic agents. Namely, these organic amine salts or quaternary ammonium salts show remarkably better pharmacokinetic properties and/or stability as compared with its free form and alkali metal salts.

Namely, the present invention provides:

(1)
An organic amine salt or a salt with quaternary ammonium ion of 3-{[((2E)-2-{1-[5-(4-t-butylphenyl)-4-hydroxy-3-thienyl]ethylidene}hydrazino)carbonothioyl]amino}benzoic acid.

(2)
The organic amine salt or the salt with quaternary ammonium ion according to (1), wherein the organic amine or quaternary ammonium salt is an organic amine or quaternary ammonium salt having a hydroxy group.

(3)
The organic amine salt or the salt with quaternary ammonium ion according to (2), wherein the organic amine or quaternary ammonium salt having a hydroxy group is ethanolamine, tromethamine or choline.

(4)
Ethanolamine salt of 3-{[((2E)-2-{1-[5-(4-t-butylphenyl)-4-hydroxy-3-thienyl]ethylidene}hydrazino)carbonothioyl]amino}benzoic acid.

(5)
Tromethamine salt of 3-{[((2E)-2-{1-[5-(4-t-butylphenyl)-4-hydroxy-3-thienyl]ethylidene}hydrazino)carbonothioyl]amino}benzoic acid.

(6)
Choline salt of 3-{[((2E)-2-{1-[5-(4-t-butylphenyl)-4-hydroxy-3-thienyl]ethylidene}hydrazino)carbonothioyl]amino}benzoic acid.

(7)
A medicine containing the organic amine salt or a salt with quaternary ammonium ion as defined in any one of (1) to (6) as an active ingredient.

(8)
The medicine according to (7), which is a thrombopoietin receptor activator.

(9)
The medicine according to (7), which is a platelet increasing agent.

(10)
A method for producing an organic amine salt or a salt with quaternary ammonium ion of 3-{[((2E)-2-{1-[5-(4-t-butylphenyl)-4-hydroxy-3-thienyl]ethylidene}hydrazino)carbonothioyl]amino}benzoic acid, which comprises reacting 3-{[((2E)-2-{1-[5-(4-t-butylphenyl)-4-hydroxy-3-thienyl]ethylidene}hydrazino)carbonothioyl]amino}benzoic acid with an organic amine or quaternary ammonium salt in a solvent.

(11)
The method according to (10), wherein the reaction is carried out at 0 to 70° C., and the resulting organic amine or quaternary ammonium salt is crystallized.

(12)
The method according to (10) or (11), wherein the organic amine or quaternary ammonium salt is ethanolamine, tromethamine or choline.

(13)
The method according to (10) or (11), wherein the organic amine is ethanol amine, and the solvent is acetonitrile.

(14)

The method according to (10) or (11), wherein the organic amine is tromethanine, the solvent is tetrahydrofuran, and after formation of the organic amine salt, the organic amine salt is crystallized by adding acetonitrile to the solvent.

(15)

The method according to (10) or (11), wherein the organic amine is tromethamine, the solvent is a solvent mixture of acetone and water, and after formation of the organic amine salt, the organic amine salt is crystallized by replacing the solvent by 1-propanol.

(16)

The method according to (10) or (11), wherein the organic amine or quaternary ammonium salt is choline, and the solvent is acetonitrile.

Advantageous Effect(s) of Invention

The organic amine salts of the present invention have properties useful as an active ingredient of medicines such as thrombopoietin receptor activators and platelet increasing agents such as excellent pharmacokinetic properties and/or stability.

DESCRIPTION OF DRAWING(S)

FIG. 1 is a graph showing the results of an oral absorption test on dogs in EXAMPLE and shows plasma concentrations—time profiles of levels of Compound A (Free Acid), the potassium salt of Compound A (Potassium Salt), the choline salt of Compound A (Choline Salt), the ethanolamine salt of Compound A (Ethanolamine Salt) and the tromethamine salt of Compound A (Tromethamine Salt).

DESCRIPTION OF EMBODIMENT(S)

In the present invention, "t" denotes tertiary.

First, Compound A in the present invention will be explained.

Compound A is 3-{[((2E)-2-{1-[5-(4-t-butylphenyl)-4-hydroxy-3-thienyl]ethylidene}hydrazino)carbonothioyl]amino}benzoic acid. Structural formula of compound A is represented by the following formula (II).

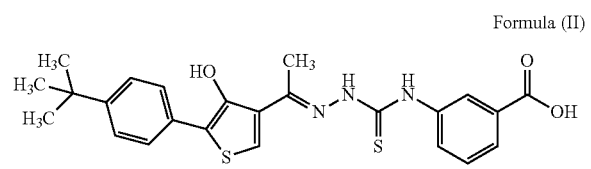 [SMILES: C/C(=N\NC(=S)Nc1cccc(C(=O)O)c1)c1csc(-c2ccc(C(C)(C)C)cc2)c1O]

Formula (II)

Compound A covers its geometrical isomers and tautomers thereof. Compound A also covers a mixture containing its geometrical isomers or tautomers thereof in an arbitrarily ratio.

Although Compound A covers 3-{[((2E)-2-{1-[5-(4-t-butylphenyl)-4-hydroxy-3-thienyl]ethylidene}hydrazino)carbonothioyl]amino}benzoic acid (E isomer) and its geometrical isomer 3-{[((2Z)-2-{1-[5-(4-t-butylphenyl)-4-hydroxy-3-thienyl]ethylidene}hydrazino)carbonothioyl]amino}benzoic acid (Z isomer), in the present invention, it is preferably the E isomer.

Next, the organic amines of the present invention will be described.

In the present invention, an organic amine means a compound derived by replacing at least one hydrogen atom(s) in ammonia by hydrocarbon group(s).

The organic amines of the present invention include primary amines having one hydrocarbon group which may have a substituent, secondary amines having two hydrocarbon groups which may have a substituent and tertiary amines having three hydrocarbon groups which may have a substituent.

A quaternary ammonium salt is in the form of a salt with a different counter anion before it forms a salt with Compound A and forms a salt with a quaternary ammonium ion of Compound A by replacing the counter anion.

The organic amine salts and the salt with quaternary ammonium ion of the present invention will be further characterized.

The organic amine salts and quaternary ammonium salts of the present invention are expressed by the following formula (I) by using ions.

$$A^- \ ^+B \qquad \text{Formula (I)}$$

$A^-$ is an n-valent organic anion derived by removing n hydrogen ions (wherein n is larger than 0 and at most 4) from Compound A, and preferred are organic anions wherein n is 1 or 2 represented by the following formula (III).

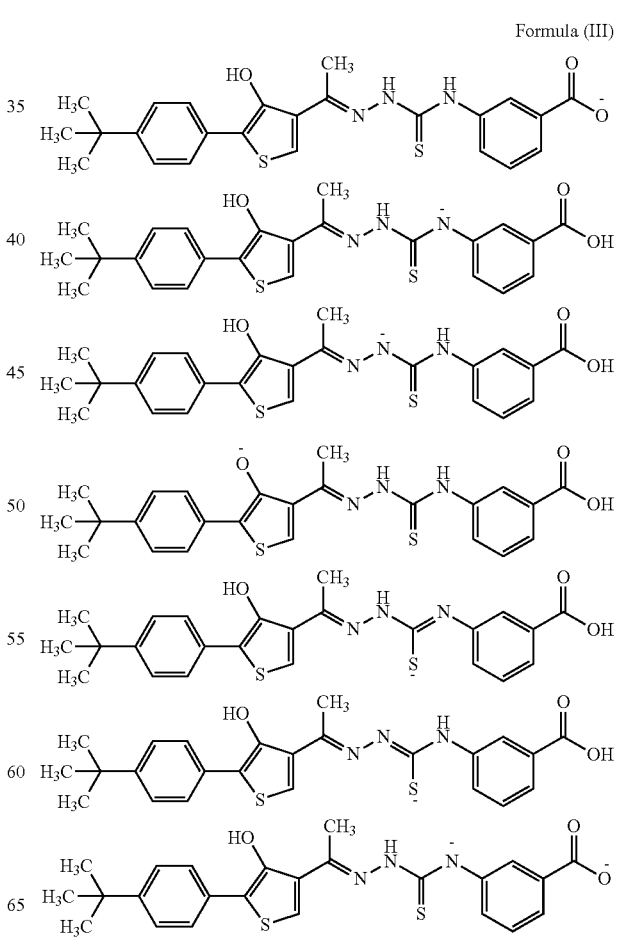

Formula (III)

-continued

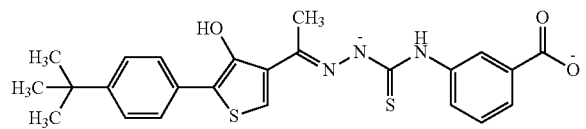
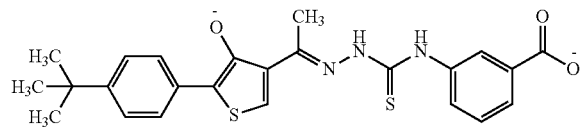
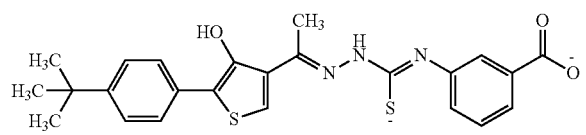
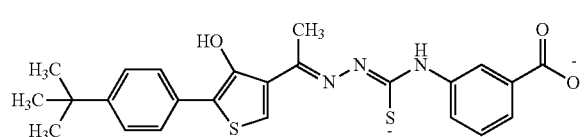
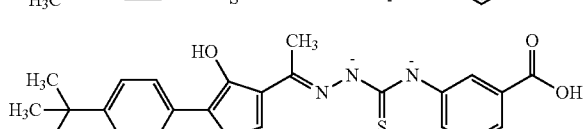
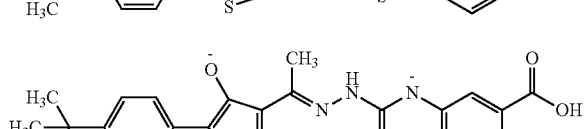
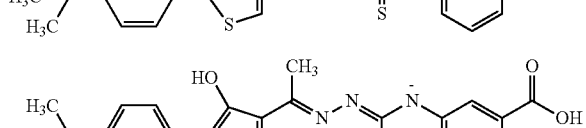
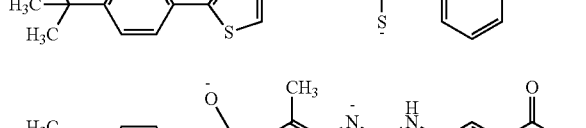
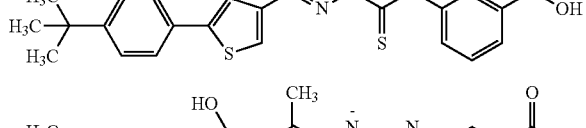
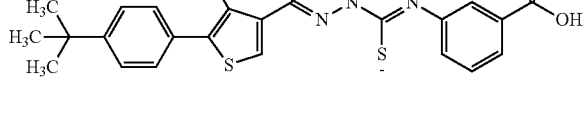
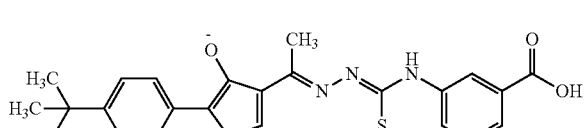
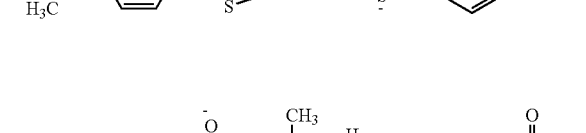
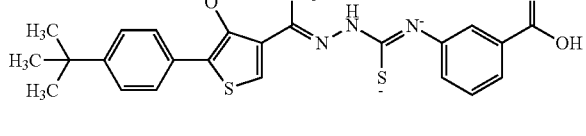

Particularly preferred are organic anions wherein n is 1 represented by the following formula (IV).

Formula (IV)

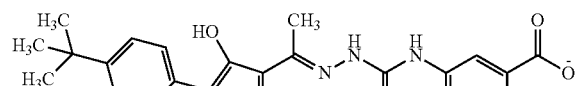
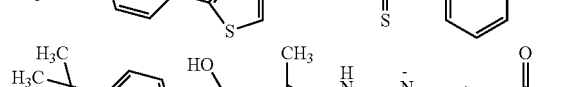
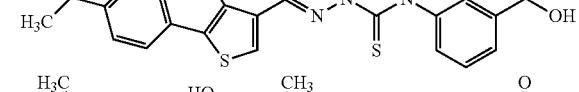
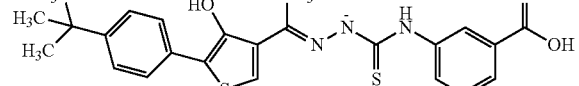
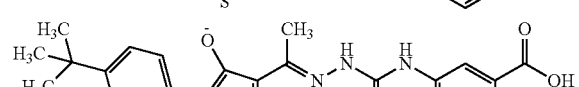
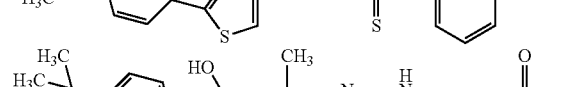
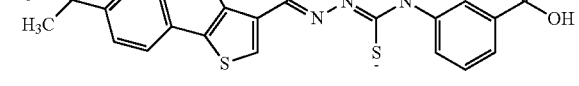
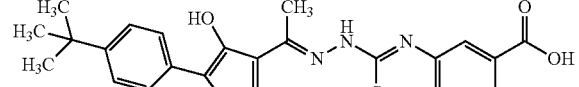

Further preferred is the organic anion represented by the following formula (V).

Formula (V)

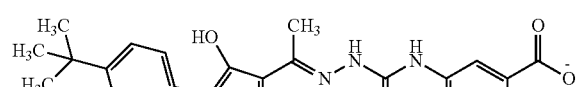

In the formula (I), B is a primary, secondary or tertiary amine having n amino groups or a n-valent quaternary ammonium salt and may be a combination of an identical organic amine, different organic amines, an identical quaternary ammonium salt and different quaternary ammonium salts. Preferred specific examples include organic amines having a hydroxy group and quaternary ammonium salts having a hydroxy group, and particularly preferred specific examples are diolamine, meglumine, ethanolamine, tromethamine and choline, and further particularly preferred specific examples are ethanolamine, tromethamine and quaternary ammonium salts having a choline cation $B^+$ is an organic ammonium cation generated by adding one hydrogen ion to each n amino groups or is the cation moiety in an n-valent quaternary ammonium salt and may be an n-valent cation which consists of combination of an identical organic ammonium cation, different organic ammonium cations, an identical cation moiety in a quaternary ammonium salt and different cation moieties in quaternary ammonium salts. Preferred specific examples are organic ammonium cations having a hydroxy group and cation moieties in quaternary ammonium salts having a hydroxy group. Particularly preferred specific examples are organic ammonium cations wherein n is 1 represented by the following formula (VI).

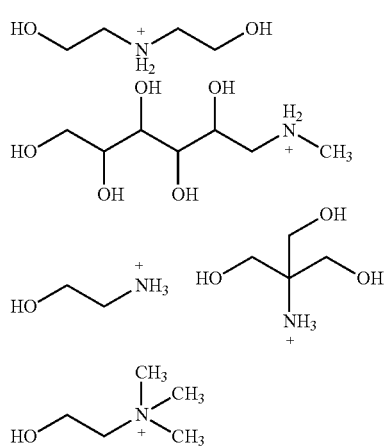

Formula (VI)

Further particularly preferred specific examples are organic ammonium cations represented by the following formula (VII).

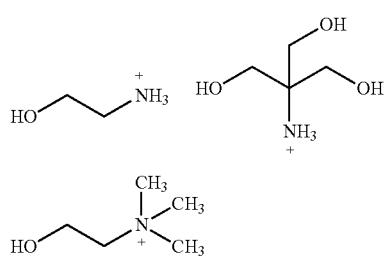

Formula (VII)

The concept of the organic amine salts and salts with quaternary ammonium ion of the present invention covers solvates of the organic amine salts and salts with quaternary ammonium ion. The solvent in such solvates can be the solvent used in production of the organic amine salts or salts with quaternary ammonium ion or accompanying them after their production. Specific examples of the solvent in such a solvate include nitrile solvents such as acetonitrile, ether solvents such as tetrahydrofuran, ketone solvents such as acetone, alcohol solvents such as methanol and water. Solvents which are likely to form solvates are acetonitrile, tetrahydrofuran, acetone, methanol, 1-propanol and water.

The solvent used in the production method of the present invention is preferably an aqueous solvent, an acetate ester or water, though any solvent that does not inhibit the reaction may be used without particular restrictions. It is more preferably acetonitrile, acetone, a solvent mixture of acetone and water, tetrahydrofuran, dimethyl sulfoxide, methanol, ethanol, 1-propanol, 2-propanol or ethyl acetate, further preferably acetonitrile, a solvent mixture of acetone and water, tetrahydrofuran or 1-propanol.

An aqueous solvent means a solvent miscible with water at any ratio.

In the method of the present invention, an organic amine or quaternary ammonium salt may be added to the reaction system in its original form without dissolving it in a solvent or in the form of a solution of the organic amine or quaternary ammonium salt. However, for industrial production, it is preferred to add the organic amine or quaternary ammonium salt in the form of a solution in view of ease of handling. The solvent in a solution of the organic amine or quaternary ammonium salt is preferably methanol, ethanol, 1-propanol, 2-propanol or water, more preferably methanol or water. Regarding the order of addition to the reaction system, the organic amine or quaternary ammonium salt may be added to a solution of Compound A, or Compound A may be added to a solution of the organic amine or quaternary ammonium salt. However, it is preferred to add the organic amine or quaternary ammonium salt to a solution of Compound A.

In the production method of the present invention, it is preferred to recover the resulting salt by crystallization in view of industrial production with easy handling and production of a product having desired properties.

For crystallization, a poor solvent may be used. The poor solvent is preferably ethyl acetate, acetonitrile, 1-propanol or 2-propanol, more preferably acetonitrile, 1-propanol or 2-propanol. The poor solvent is preferably added gradually in small portions. Use of a solvent which dissolves well Compound A, and the organic amine or quaternary ammonium salt but hardly dissolves the resulting organic amine salt or salt with quaternary ammonium ion enables the product to crystallize at the same time as its formation and to be recovered as crystals.

For crystallization, seed crystals may be added. Seed crystals can be obtained by methods well known in the art, for example, by rubbing the inner wall of a vessel containing a solution of the compound of interest with a spatula.

Specifically, when the organic amine or quaternary ammonium salt is ethanolamine or choline, it is possible to obtain the ehanolamine salt or choline salt of Compound A as crystals by using acetonitrile as the solvent. When the organic amine is tromethamine, it is possible to crystallize the tromethamine salt of Compound A by using tetrahydrofuran as the solvent and adding acetonitrile to the solvent after formation of the salt or by using a solvent mixture of acetone and water and replacing the solvent mixture with 1-propanol after formation of the salt.

The reaction between Compound A and the organic amine or quaternary ammonium salt may be carried out in a reaction solution or suspension at a temperature between the freezing point and the boiling point of the solvent at which the reaction proceeds, preferably at an inner temperature of from −78° C. to 80° C., more preferably at an inner temperature of from 0° C. to 70° C., particularly preferably at an inner temperature of from 10° C. to 60° C. The crystallization of the organic amine salt or the salt with quaternary ammonium ion may be carried out in a solution or suspension at a temperature of the freezing point and boiling point of the solvent at which crystallization proceeds, preferably at an inner temperature of −78° C. to 50° C., more preferably at an inner temperature of from −10° C. to 40° C., particularly preferably at an inner temperature of from 0° C. to 30° C.

Compound A and the organic amine or quaternary ammonium may be reacted for any period of time as long as decomposition does not occur, but the reaction time is preferably from 1 minute to 5 hours, more preferably from 1 minute to 3 hours. In order to crystallize the organic amine salt or the salt with quaternary ammonium ion, the salt may be stirred for any period of time as long as decomposition does not occur and crystallization proceeds, but the stirring time is preferably from 1 hour to 48 hours, more preferably from 2 hours to 24 hours.

In the method of the present invention, as the starting material, a solvate of Compound A may be used. Specific examples of such a solvate include solvates with methanol, 2-propanol, 2-butanol and the like.

Specific examples of the medicine of the present invention include oral medicines such as tablets, capsules, powder, granules, pills and syrup, rectal medicines, percutaneous medicines and injections.

The medicine of the present invention may be used in combination with other therapeutic agent and may be administered as a mixed agent.

The medicine of the preset invention contains an organic amine salt or a salt with quaternary ammonium ion of Compound A as an active ingredient.

The medicine of the present invention may consists of an organic salt or a salt with quaternary ammonium ion of Compound A alone. However, the medicine of the present invention is preferably a composition containing an organic amine salt or a salt with quaternary ammonium ion of Compound A as an active ingredient and other components.

Such compositions may be prepared by conventional methods by therapeutically acceptable vehicles. Namely, for oral medicines, ordinary vehicles such as excipients, lubricants, binders, disintegrants, humectants, plasticizers and coating agents may be used. Oral liquid preparations may be in the form of aqueous or oily suspensions, solutions, emulsions, syrups or elixirs or may be supplied as dry syrups to be mixed with water or other appropriate solvents before use. Such liquid preparations may contain ordinary additives such as suspending agents, perfumes, diluents and emulsifiers. In the case of rectal administration, they may be administered as suppositories. Suppositories may use an appropriate substance such as cacao butter, laurin tallow, Macrogol, glycerogelatin, Witepsol, sodium stearate and mixtures thereof as the base and may, if necessary, contain an emulsifier, a suspending agent, a preservative and the like. For injections, pharmaceutical ingredients such as distilled water for injection, physiological saline, 5% glucose solution, propylene glycol and other solvents or solubilizing agents, a pH regulator, an isotonizing agent and a stabilizer may be used to form aqueous dosage forms or dosage forms which need dissolution before use.

The concept of "the medicine containing the organic amine salt or the salt with quaternary ammonium ion as an active ingredient" of the present invention may also referred to as "organic amine salts or salts with quaternary ammonium ion for use as medicines" or "a method for treatment by using organic amine salts or salts with quaternary ammonium ion".

When the medicine is a thrombopoietin receptor activator, the present invention may also be referred to as "organic amine salts or salts with quaternary ammonium ion for use as thrombopoietin receptor activators" or "a method for treatment by activating the thrombopoietin receptor with an organic amine salt or a salt with quaternary ammonium ion".

When the medicine is a platelet increasing agent, the present invention may also be referred to as "organic amine salts or salts with quaternary ammonium ion for use as platelet increasing agents" or "a method for treatment by increasing platelets with an organic amine salt or a salt with quaternary ammonium ion".

When the medicine is a therapeutic agent for thrombocytopenia, the present invention may also be described as "organic amine salts or salts with quaternary ammonium ion for use as therapeutic agents for thrombocytopenia" or "a method for treating thrombocytopenia by using an organic amine salt or a salt with quaternary ammonium ion".

The dose of the medicine of the present invention for administration to human is usually about from 0.1 to 1000 mg/human/day in the case of oral drugs or rectal administration and about from 0.05 mg to 500 mg/human/day in the case of injections, though it depends on the age and conditions of the patient. The above-mentioned ranges are mere examples, and the dose should be determined from the conditions of the patient.

The organic amine salts or salts with quaternary ammonium ion of the present invention and medicines containing the organic amine salt or the salt with quaternary ammonium ion as active ingredients are used when the use of a compound which have thrombopoietin receptor affinity and act as thrombopoietin receptor agonists are expected to improve pathological conditions., namely prevent, treat or improve diseases against which activation of the thrombopoietin receptor is effective. Specific examples of such diseases include hematological disorders accompanied by abnormal platelet counts. Specifically, they are effective for therapy or prevention of human and mammalian diseases caused by abnormal megakaryopoiesis, especially those accompanied by thrombocytopenia. Examples of such diseases include thrombocytopenia accompanying chemotherapy and/or radiotherapy of cancer, thrombocytopenia accompanying antiviral therapy for diseases such as hepatitis C, thrombocytopenia caused by bone marrow transplantation, surgery and serious infections, or gastrointestinal bleeding, but such diseases are not restricted to those mentioned. Typical thrombocytopenias such as aplastic anemia, idiopathic thrombocytopenic purpura, myelodysplastic syndrome, hepatic disease, HIV infection and thrombopoietin deficiency are also targets of the medicine of the present invention. The present invention may be used as a peripheral stem cell mobilizer, a megakaryoblastic or megakaryocytic leukemia cell differentiation inducer and a platelet increasing agent for platelet donors. In addition, potential applications include therapeutic angiogenesis based on differentiation and proliferation of vascular endothelial cells and endothelial progenitor cells, prevention and therapy of arteriosclerosis, myocardial infarction, unstable angina, peripheral artery occlusive disease, but there is no restriction.

EXAMPLES

Now, the present invention will be described in further detail with reference to Synthetic Examples, Assay Examples and Formulation Examples. However, it should be understood that the present invention is by no means restricted by these specific Examples.

In the Examples, LC denotes liquid chromatography, HPLC denotes high performance liquid chromatography, MS denotes mass spectrometry, LC/MS denotes liquid chromatography-mass spectrometry, LC/MS/MS denotes liquid chromatography-tandem mass spectrometry, TG denotes thermogravimetry, Cmax denotes maximum plasma concentration, Tmax denotes time to maximum plasma concentration, and AUC denotes area under the plasma concentration-time curve.

The instrumental analyses were carried out under the following conditions with the following instruments.

$^1$H-NMR was measured at 300 MHz.

TG was performed by using TG8120 (Rigaku Corporation).

Reference Synthetic Example 1

3-{[((2E)-2-{1-[5-(4-t-Butylphenyl)-4-hydroxy-3-thienyl]ethylidene}hydrazine)carbonothioyl]amino}benzoic acid 3-{[((2E)-2-{1-[5-(4-t-Butylphenyl)-4-hydroxy-3-thienyl]ethylidene}hydrazine)carbonothioyl]amino}benzoic acid was prepared in accordance with US 2006094694.

Reference Synthetic Example 2

Potassium 3-{[((2E)-2-{1-[5-(4-t-butylphenyl)-4-hydroxy-3-thienyl]ethylidene}hydrazine)carbonothioyl]amino}benzoate Potassium 3-{[((2E)-2-{1-[5-(4-t-butylphenyl)-4-hydroxy-3-thienyl]ethylidene}hydrazine)carbonothioyl]amino}benzoate was prepared in accordance with US 2006094694.

Synthetic Example 1

Ethanolamine salt of 3-{[((2E)-2-{1-[5-(4-t-butylphenyl)-4-hydroxy-3-thienyl]ethylidene}hydrazino)carbonothioyl]amino}benzoic acid A suspension of 3-{[((2E)-2-{1-[5-(4-t-butylphenyl)-4-hydroxy-3-thienyl]ethylidene}hydrazino)carbonothioyl]amino}benzoic acid (10.25 g, 21.92 mmol) in acetonitril (218 mL) was stirred with a solution of ethanol amine (1.47 g, 24.07 mmol) in methanol (24.0 mL) at room temperature for 2 hours and 50 minutes. The resulting precipitate was collected by filtration, washed with acetonitrile and dried under reduced pressure to obtain 10.88 g of the desired product (yield 94%).

Morphology: pale yellow solid $^1$H-NMR (300 MHz, DMSO-$d_6$): δ 1.30 (9H, s), 2.39 (3H, s), 2.84 (2H, t, J=5.0 Hz), 3.56 (2H, t, J=5.0 Hz), 7.27 (1H, dd, J=8.0&7.5 Hz), 7.40 (2H, d, J=8.5 Hz), 7.46 (1H, d, J=7.5 Hz), 7.62 (1H, s), 7.73 (2H, d, J=8.5 Hz), 7.91 (1H, d, J=8.0 Hz), 8.50 (1H, s)

Synthetic Example 2

Tromethamine salt of 3-{[((2E)-2-{1-[5-(4-t-butylphenyl)-4-hydroxy-3-thienyl]ethylidene}hydrazino)carbonothioyl]amino}benzoic acid A solution of 3-{[((2E)-2-{1-[5-(4-t-butylphenyl)-4-hydroxy-3-thienyl]ethylidene}hydrazino)carbonothioyl]amino}benzoic acid (9.4 g, 20.1 mmol) in tetrahydrofuran (100 mL) was stirred with an aqueous solution (20 mL) of tromethamine (2.7 g, 22.3 mmol) and then with acetonitrile (400 mL) and stirred at room temperature for 1 day. The resulting precipitate was collected by filtration, washed with acetonitrile and dried under reduced pressure to obtain 11.3 g of the desired product (yield 95%).

Morphology: white to pale yellow green solid $^1$H-NMR (300 MHz, DMSO-$d_6$): δ 1.30 (9H, s), 2.38 (3H, s), 3.45 (6H, s), 7.29 (1H, dd, J=8.0&7.5 Hz), 7.40 (2H, d, J=8.5 Hz), 7.47 (1H, d, J=7.5 Hz), 7.64 (1H, s), 7.72 (2H, d, J=8.5 Hz), 7.89 (1H, d, J=8.0 Hz), 8.51 (1H, s)

Synthetic Example 3

Tromethamine salt of 3-{[((2E)-2-{1-[5-(4-t-butylphenyl)-4-hydroxy-3-thienyl]ethylidene}hydrazino)carbonothioyl]amino}benzoic acid A solution of 3-{[((2E)-2-{1-[5-(4-t-butylphenyl)-4-hydroxy-3-thienyl]ethylidene}hydrazino)carbonothioyl]amino}benzoic acid (4.7 g, 10.0 mmol) in a mixture of acetone (130 mL) and water (5.2 mL) was stirred with an aqueous solution (4.7 mL) of tromethamine (1.27 g, 10.5 mmol) at 50° C. for 30 minutes. The solvent was replaced by 1-propanol, and the resulting precipitate was collected by filtration and dried under reduced pressure to obtain 5.14 g of the desired product (yield 91%).

Morphology: pale yellow solid

Synthetic Example 4

Choline salt of 3-{[((2E)-2-{1-[5-(4-t-butylphenyl)-4-hydroxy-3-thienyl]ethylidene}hydrazino)carbonothioyl]amino}benzoic acid A suspension of 3-{[((2E)-2-{1-[5-(4-t-butylphenyl)-4-hydroxy-3-thienyl]ethylidene}hydrazino)carbonothioyl]amino}benzoic acid (9.40 g, 20.11 mmol) in acetonitrile (300 mL) was stirred with 3.5 M solution of choline in methanol (6.11 mL, 21.39 mmol) at room temperature for 40 minutes, and then with seed crystals (about 10 mg) at room temperature for 15 hours. The resulting precipitate was collected by filtration, washed with acetonitrile and dried under reduced pressure to obtain 10.05 g of the desired product (yield 82.3%).

Morphology: pale yellow solid $^1$H-NMR (300 MHz, DMSO-$d_6$): δ 1.30 (9H, s), 2.39 (3H, s), 3.10 (9H, s), 3.37-3.40 (2H, m), 3.80-3.85 (2H, m), 7.24 (1H, dd, J=8.1&7.5 Hz), 7.38-7.41 (3H, m), 7.55 (1H, s), 7.74 (2H, d, J=8.4 Hz), 7.92 (1H, d, J=8.1 Hz), 8.61 (1H, s)

Assay Example 1

Oral Absorption Test on Dogs

The free form (Compound A), potassium salt, organic amine salts (ethanolamine salt and tromethamine salt) and salt of quaternary ammonium ion (choline salt) of 3-{[((2E)-2-{1-[5-(4-t-butylphenyl)-4-hydroxy-3-thienyl]ethylidene}hydrazino)carbonothioyl]amino}benzoic acid in capsule were orally administered to beagle dogs at a dose of 360 mg/dog. 0.5, 1, 2, 4, 6, 8 and 24 hours after the administration, blood was collected to obtain plasma samples. Their concentrations in dog plasma were measured by LC/MS/MS. Using the plasma concentrations obtained, maximum plasma concentration (Cmax), time to maximum plasma concentration (Tmax) and area under the plasma concentration-time curve were calculated. FIG. 1 shows the plasma concentrations—time profiles of Compound A, the potassium salt and various organic amine salts and quaternary ammonium salt after oral administration to dogs at a dose of 360 mg/dog.

In FIG. 1, * represents Compound A (Free Acid), ♦ represents the potassium salt (Potassium Salt), □ represents the choline salt (Choline Salt), ▲ represents ethanolamine (Ethanolamine Salt), and ○ represents the tromethamine salt (Tromethamine Salt).

The organic amine salts and the salt of quaternary ammonium ion of the present invention showed much better pharmacokinetic properties than Compound A and the potassium salt disclosed in WO04/108683. Namely, in terms of maximum plasma concentration, while the potassium salt was 7.2 times better than Compound A, the organic amine salts and the salt of quaternary ammonium ion of the present invention showed marked improvements and were from 1.7 to 2.2 times better than the potassium salt and from 12.0 to 15.7 times better than Compound A. In terms of area under the plasma concentration-time curve, while the potassium salt was 6.3 times better than Compound A, the organic amine salts and the salt of quaternary ammonium ion of the present invention showed remarkable improvements and were from 2.9 to 4.4 times better than the potassium salt and from 18.4 to 27.6 times better than Compound A. The remarkably improved pharmacokinetic properties, as described above, of the organic amine salts and the salt of quaternary ammonium ion (especially the choline salt, ethanolamine salt and tromethamine salt) were unexpectable even to people skilled in the art, and the data demonstrate the usefulness of the present invention.

In the following Assay Examples 2 to 4, the stability of the ethanolamine salt (1), tromethamine salt (2), choline salt (3) and potassium salt (4) of 3-{[((2E)-2-{1-[5-(4-t-butylphenyl)-4-hydroxy-3-thienyl]ethylidene}hydrazino)carbonothioyl]amino}benzoic acid to temperature, humidity and light was evaluated, by related substance increase (%), weight change (%) or TG loss change (%) through appropriate selection.

Related substance increase (%)

Each sample was analyzed by high performance liquid chromatography before and after treatment, and the sum of area percentages for analogues in each sample were calculated.

Column: L-column ODS (Chemicals Evaluation and Research Institute, Japan inner diameter 4.6 mm, length 250 mm)
Detector: UV absorptiometer (wavelength; 254 m)
Column temperature: 40° C.
Flow rate: 1.0 mL/min
Injection volume: 10 μL
Mobile phase: (a) 0.01 M ammonium formate buffer (pH 3.0)
(b) acetonitrile
Measurements were carried out with a gradient between the above (a) and (b) solutions.

An increase in related substances from the initial value suggests possibility of compound degradation, and hence related substances increase is an indication of stability of a compound.

Weight change (%);

Each sample was weighed before and after treatment, and weight gain was calculated in percentages from the difference in weight. The magnitude of weight change during treatment is an indication of stability of a compound. TG loss change (%);

About 5 mg of each sample was weighed out before and after treatment and put in an aluminum pan, and TG measurements were performed with the pan left open. The rate of TG loss of each sample was calculated in percentages (%). The measuring conditions are shown below.

Measuring Conditions;
Instrument:TG8120 (Rigaku Corporation)
Measuring range: room temperature to 105° C.
Heating rate: 5° C./min
Atmosphere: air 50 mL/min An increase in TG loss from the initial value indicates possibility of moisture absorption and degradation of a compound. Therefore, the magnitude of change in TG loss is an indication of stability of a compound.

The initial values of TG loss and related substances for each sample are shown in Table 1.

TABLE 1

|  | (1) | (2) | (3) | (4) |
|---|---|---|---|---|
| Related substances (%) | 0.34 | 0.07 | 0.34 | 1.86 |
| TG loss (%) | 0.64 | 0.11 | 1.19 | 3.18 |

Assay Example 2

Thermal Stability Test

The thermal stability of the ethanolamine salt (1), tromethamine salt (2), choline salt (3) and potassium salt (4) of 3-{[((2E)-2-{1-[5-(4-t-butylphenyl)-4-hydroxy-3-thienyl]ethylidene}hydrazino)carbonothioyl]amino}benzoic acid was evaluated as follows.
(Treatment)

Each sample was put in a brown glass vessel, and the vessel was left at 60° C. for 2 weeks without humidity control. After 2 weeks, the sample was withdrawn, and the related substance increase (%) was evaluated.

The results are shown in Table 2.

TABLE 2

|  | (1) | (2) | (3) | (4) |
|---|---|---|---|---|
| Related substance increase | 0.16 | −0.01 | −0.01 | 2.46 |

The organic amine salts and quaternary ammonium salt of the present invention showed a much less related substance increases than the potassium salt and remarkable stability under the conditions used in the thermal stability test.

Assay Example 3

Hygrostability Test

The hygrostability of the ethanolamine salt (1), tromethamine salt (2), choline salt (3) and potassium salt (4) of 3-{[((2E)-2-{1-[5-(4-t-butylphenyl)-4-hydroxy-3-thienyl]ethylidene}hydrazino)carbonothioyl]amino}benzoic acid was evaluated as follows.
(Treatment)

About 1 g of each sample was put in a transparent glass vessel and maintained at 25° C./90% RH (relative humidity) for 2 weeks with the vessel left open. After 2 weeks, the sample was withdrawn, and the related substance increase (%), weight change (%) and TG loss change (%) were evaluated.

The results are shown in Table 3.

TABLE 3

|  | (1) | (2) | (3) | (4) |
|---|---|---|---|---|
| Related substance increase | 0.04 | −0.03 | −0.01 | 0.39 |
| Weight change | 0.29 | 0.00 | 0.10 | 23.22 |
| TG loss change | −0.26 | −0.13 | 0.66 | 7.86 |

The organic amine salts and quaternary ammonium salt of the present invention showed much less related substance increases, weight changes and TG loss change than the potassium salt and remarkable stability under the conditions used in the hygrostability. The data show that the organic amine salts and quaternary ammonium salt of the present invention are quite useful as compared with the potassium salt.

Assay Example 4

Photostability Test

The photostability of the ethanolamine salt (1), tromethamine salt (2), choline salt (3) and potassium salt (4) of 3-{[((2E)-2-{1-[5-(4-t-butylphenyl)-4-hydroxy-3-thienyl]ethylidene}hydrazino)carbonothioyl]amino}benzoic acid was evaluated as follows.

(Treatment)

About 1 g of each sample was put in a transparent glass vessel at 25° C./60% RH (relative humidity) with the vessel left open and irradiated with light of 200 W·hr·m$^2$ for 57 hours. After 2 weeks, the sample was withdrawn, and the related substance increase (%), weight change (%) and TG loss change (%) were evaluated. The results are shown in Table 4.

TABLE 4

|  | (1) | (2) | (3) | (4) |
| --- | --- | --- | --- | --- |
| Related substance increase | −0.01 | 0.01 | 0.00 | 0.27 |
| Weight change | 0.23 | 0.01 | 0.17 | 9.36 |
| TG loss change | −0.25 | −0.13 | 0.58 | 3.16 |

The organic amine salts and quaternary ammonium salt of the present invention showed much less related substance increases, weight changes and TG loss change than the potassium salt and remarkable stability under the conditions used in the photostability test.

Formulation Example 1

A granule preparation containing the following ingredients is prepared.

| Ingredients | |
| --- | --- |
| Compound represented by the formula (I) | 10 mg |
| Lactose | 700 mg |
| Corn Starch | 274 mg |
| HPC-L | 16 mg |
| | 1000 mg |

A compound represented by the formula (I) and lactose are sifted through a 60-mesh sieve. Corn starch is sifted through a 120-mesh sieve. They are mixed in a V-type blender. The powder mixture is kneaded with a low-viscosity hydroxypropylcellulose (HPC-L) aqueous solution, granulated (extrusion granulation, die size 0.5-1 mm) and dried. The resulting dry granules are sifted through a shaking sieve (12/60 mesh) to obtain a granule preparation.

Formulation Example 2

A powder preparation for capsulation containing the following ingredients is prepared.

| Ingredients | |
| --- | --- |
| Compound represented by the formula (I) | 10 mg |
| Lactose | 79 mg |
| Corn Starch | 10 mg |
| Magnesium Stearate | 1 mg |
| | 100 mg |

A compound represented by the formula (I) and lactose are sifted through a 60-mesh sieve. Corn starch is sifted through a 120-mesh sieve. They are mixed with magnesium stearate in a V-type blender. The 10% powder is put in hard gelatin capsules No. 5, 100 mg each.

Formulation Example 3

A granule preparation for capsulation containing the following ingredients is prepared.

| Ingredients | |
| --- | --- |
| Compound represented by the formula (I) | 15 mg |
| Lactose | 90 mg |
| Corn Starch | 42 mg |
| HPC-L | 3 mg |
| | 150 mg |

A compound represented by the formula (I) and lactose are sifted through a 60-mesh sieve. Corn starch is sifted through a 120-mesh sieve. They are mixed in a V-type blender. The powder mixture is kneaded with a low-viscosity hydroxypropylcellulose (HPC-L) aqueous solution, granulated and dried. The resulting dry granules are sifted through a shaking sieve (12/60 mesh). The granules are put in hard capsules No. 4, 150 mg each.

Formulation Example 4

A tablet preparation containing the following ingredients is prepared.

| Ingredients | |
| --- | --- |
| Compound represented by the formula (I) | 10 mg |
| Lactose | 90 mg |
| Microcrystalline cellulose | 30 mg |
| Magnesium Stearate | 5 mg |
| CMC-Na | 15 mg |
| | 150 mg |

A compound represented by the formula (I), lactose, microcrystalline cellulose and CMC-Na (carboxymethylcellulose sodium salt) are sifted through a 60-mesh sieve and mixed. The powder mixture is mixed with magnesium stearate to give a bulk powder mixture. The powder mixture is compressed directly into 150 mg tablets.

Formulation Example 5

An intravenous preparation is prepared as follows.

| Compound represented by the formula (I) | 100 mg |
| Saturated Fatty Acid Glyceride | 1000 ml |

Solutions having the above-mentioned composition are usually administered to a patient intravenously at a rate of 1 ml per 1 minute.

Industrial Applicability

The organic amine salts and the salts with quaternary ammonium ion of the present invention are useful as active ingredients of medicines such as thrombopoietin receptor activators and platelet increasing agents.

The entire disclosure of Japanese Patent Application No. 2010-246632 filed on Nov. 2, 2010 including specification, claims, abstract and drawings is incorporated herein by reference in its entirety.

The invention claimed is:

1. A salt of 3-{[((2E)-2-{1-[5-(4-t-butylphenyl)-4-hydroxy-3-thienyl]ethylidene}hydrazino)carbonothioyl]amino}benzoic acid, which is selected from the group consisting of:
   an ethanolamine salt of 3-{[((2E)-2-{1-[5-(4-t-butylphenyl)-4-hydroxy-3-thienyl]ethylidene}hydrazino)carbonothioyl]aminol}benzoic acid;
   a tromethamine salt of 3-{[((2E)-2-{1-[5-(4-t-butylphenyl)-4-hydroxy-3-thienyl]ethylidene}hydrazino)carbonothioyl]aminol}benzoic acid; and
   a choline salt of 3-{[((2E)-2-{1-[5-(4-t-butylphenyl)-4-hydroxy-3-thienyl]ethylidene}hydrazino)carbonothioyl]amino}benzoic acid.

2. An ethanolamine salt of 3-{[((2E)-2-{1-[5-(4-t-butylphenyl)-4-hydroxy-3-thienyl]ethylidene}hydrazino)carbonothioyl]amino}benzoic acid.

3. A tromethamine salt of 3-{[((2E)-2-{1-[5-(4-t-butylphenyl)-4-hydroxy-3-thienyl]ethylidene}hydrazino)carbonothioyl]-amino}benzoic acid.

4. A choline salt of 3-{[((2E)-2-{1-[5-(4-t-butylphenyl)-4-hydroxy-3-thienyl]ethylidene}hydrazino)carbonothioyl]amino}benzoic acid.

5. A medicine, comprising a salt according to claim 1 as an active ingredient.

6. A method for producing an organic amine salt of 3-{[((2E)-2-{1-[5-(4-t-butylphenyl)-4-hydroxy-3-thienyl]ethylidene}hydrazino)carbonothioyl]amino}benzoic acid,
   said method comprising reacting 3-{[((2E)-2-{1-[5-(4-t-butylphenyl)-4-hydroxy-3thienyl]ethylidene}hydrazino)carbonothioyl]amino}benzoic acid with an organic amine, in a solvent,
   wherein said organic amine is ethanolamine and said solvent is acetonitrile.

7. The method according to claim 6, wherein said reacting is carried out at a temperature of 0 to 70° C., and said organic amine salt is crystallized.

8. A method for producing an organic amine salt of 3-{[((2E)-2-{1-[5-(4-t-butylphenyl)-4-hydroxy-3-thienyl]ethylidene}hydrazino)carbonothioyl]amino}benzoic acid,
   said method comprising reacting 3-{[((2E)-2-{1-[5-(4-t-butylphenyl)-4-hydroxy-3-thienyl]ethylidene}hydrazino)carbonothioyl]amino}benzoic acid with an organic amine, in a solvent,
   wherein said organic amine is tromethamine and said solvent is tetrahydrofuran, and
   after formation of said organic amine salt, crystallizing said organic amine salt by adding acetonitrile to said tetrahydrofuran.

9. The method according to claim 8, wherein said reacting is carried out at a temperature of 0 to 70° C.

10. A method for producing an organic amine salt of 3-{[((2E)-2-{1-[5-(4-t-butylphenyl)-4-hydroxy-3-thienyl]ethylidenel}hydrazino)carbonothioyl]amino}benzoic acid,
    said method comprising reacting 3-{[((2E)-2-{1-[5-(4-t-butylphenyl)-4-hydroxy-3thienyl]ethylidene}hydrazino)carbonothioyl]amino}benzoic acid with an organic amine, in a solvent,
    wherein said organic amine is tromethamine and said solvent is a mixture of acetone and water, and
    after formation of said organic amine salt, crystallizing said organic amine salt by replacing said mixture of acetone and water with 1-propanol.

11. The method according to claim 10, wherein said reacting is carried out at a temperature of 0 to 70° C.

12. A method for producing an organic amine salt of 3-{[((2E)-2-{1-[5(4-t-butylphenyl)-4-hydroxy-3-thienyl]ethylidene}hydrazino)carbonothioyl]amino}benzoic acid,
    said method comprising reacting 3-{[((2E)-2-{1-[5-(4-t-butylphenyl)-4-hydroxy-3-thienyl]ethylidene}hydrazino)carbonothioyl]amino}benzoic acid with an organic amine, in a solvent,
    wherein said organic amine is choline and said solvent is acetonitrile.

13. The method according to claim 12, wherein said reacting is carried out at a temperature of 0 to 70° C., and said organic amine salt is crystallized.

14. A pharmaceutical composition, comprising a salt according to claim 1 and at least one pharmaceutically acceptable excipient.

15. A method of treating thrombocytopenia, comprising administering effective amount of a salt according to claim 1 to a subject in need thereof.

16. A method of treating thrombocytopenia, comprising administering an effective amount of the salt according to claim 2 to a subject in need thereof.

17. A method of treating thrombocytopenia, comprising administering effective amount of the salt according to claim 3 to a subject in need thereof.

18. A method of treating thrombocytopenia, comprising administering effective amount of the salt according to claim 4 to a subject in need thereof.

* * * * *